United States Patent [19]

Percival et al.

[11] 4,146,646

[45] Mar. 27, 1979

[54] BIS-AMIDE FUNGICIDAL COMPOUNDS

[75] Inventors: Albert Percival, Cambridge; Peter J. Burton, Stortford, both of England

[73] Assignee: Fisons Limited, London, England

[21] Appl. No.: 763,118

[22] Filed: Jan. 27, 1977

[30] Foreign Application Priority Data

Feb. 12, 1976 [GB] United Kingdom .............. 5515/76

[51] Int. Cl.$^2$ .................... A01N 9/20; A01N 9/24
[52] U.S. Cl. ............................ 424/324; 424/304; 424/320
[58] Field of Search ............... 424/320, 324, 304; 260/551 R, 558 R

[56] References Cited

U.S. PATENT DOCUMENTS

| | | | |
|---|---|---|---|
| 2,742,501 | 4/1956 | Kleine et al. ............... | 260/558 R |
| 3,085,940 | 4/1963 | Tomcufcik et al. .......... | 424/320 |
| 3,085,941 | 4/1963 | Tomcufcik et al. .......... | 424/320 |
| 3,520,927 | 7/1970 | Malz et al. .................. | 424/324 |
| 3,565,993 | 2/1971 | Hamm ......................... | 424/320 |
| 3,707,477 | 12/1972 | Ost et al. ..................... | 424/320 |
| 3,869,443 | 3/1975 | Lesher ......................... | 260/558 R |
| 3,923,494 | 12/1975 | Teach .......................... | 260/558 R |

FOREIGN PATENT DOCUMENTS

| | | | |
|---|---|---|---|
| 44-16397 | 7/1969 | Japan ............................ | 424/320 |
| 1256197 | 8/1971 | United Kingdom. | |

*Primary Examiner*—Albert T. Meyers
*Assistant Examiner*—D. W. Robinson
*Attorney, Agent, or Firm*—Wenderoth, Lind & Ponack

[57] ABSTRACT

Bis-amides of formula

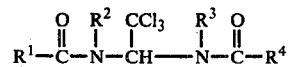

and salts thereof, where $R^2$ and $R^3$ are hydrogen; alkyl of up to 9 carbon atoms, alkenyl or alkynyl of up to 4 carbon atoms, or aryl, groups optionally substituted by certain radicals; or cycloalkyl of 3–7 carbon atoms; and $R^1$ and $R^4$ are as $R^2$ and $R^3$ or amino groups optionally substituted by certain radicals, are fungicides, especially against soil borne fungal diseases of plants.

20 Claims, No Drawings

BIS-AMIDE FUNGICIDAL COMPOUNDS

This invention relates to chloral derivatives, otherwise denominated bis-amide compounds.

The invention provides a method of combating fungus at a locus infested or liable to be infested with it, which method comprises applying to the locus a fungus-combating amount of a compound which is a chloral derivative of formula

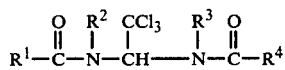

or a salt thereof:

wherein $R^1$ and $R^4$ are the same or different and each represents hydrogen; alkyl of up to 9 carbon atoms (preferably up to 6 carbon atoms e.g. methyl) optionally substituted by one or more substituents selected from halogen, nitro, hydroxy and cyano; alkeny of up to 4 carbon atoms (e.g. allyl) optionally substituted by one or more halogen atoms; alkynyl of up to 4 carbon atoms (e.g. propargyl) optionally substituted by one or more halogen atoms; cycloalkyl of 3–7 carbon atoms (e.g. cyclohexyl); aryl (preferably phenyl) optionally substituted by one or more substituents selected from halogen, nitro, alkoxy of 1–4 carbon atoms (e.g. methoxy) and alkyl of 1–4 carbon atoms (e.g. methyl or t-butyl) optionally substituted by one or more halogen atoms; a heterocyclic radical (preferably furyl) optionally substituted by one or more substituents selected from halogen, alkyl of 1–4 carbon atoms and nitro; or amino optionally substituted by one or two substituents selected from alkyl of 1–6 carbon atoms (preferably methyl), and phenyl optionally substituted by one or more substituents selected from halogen, nitro and alkyl of 1–4 carbon atoms (e.g. methyl) optionally substituted by one or more halogen atoms; and $R^2$ and $R^3$ are the same or different and each represents hydrogen; alkyl of up to 9 carbon atoms (preferably up to 6 carbon atoms e.g. methyl) optionally substituted by one or more substituents selected from halogen, nitro, hydroxy and cyano; cycloalkyl of 3–7 carbon atoms (e.g. cyclohexyl); alkenyl of 2–4 carbon atoms (e.g. allyl) optionally substituted by one or more halogen atoms; alkynyl of 2–4 carbon atoms (e.g. propargyl) optionally substituted by one or more halogen atoms; or aryl (preferably phenyl) optionally substituted by one or more substituents selected from halogen, nitro, alkoxy of 1–4 carbon atoms (e.g. methoxy) and alkyl of 1–4 carbon atoms (e.g. methyl) optionally substituted by one or more halogen atoms.

The invention provides also a fungicidal composition containing the compound, usually 0.01–80% of the compound, particularly a fungicidal composition comprising the compound together with at least one material selected from solid carriers, liquid carriers which are hydrocarbons of boiling point within the range 130°–270° C., surface active agents and other pesticides.

The invention also provides a process for preparing the compound of formula I, which process comprises acylating an amine of formula

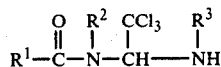

or a salt thereof (e.g. with alkalis or acids, such as an alkali metal e.g. sodium salt or a hydrochloride salt) wherein $R^1$, $R^2$ and $R^3$ are as in formula I, with an acid chloride or anhydride of formula $R^4COCl$ or $(R^4CO)_2O$ wherein $R^4$ is as in formula I.

The invention provides also a process for preparing the compound of formula I in which $R^4$ represents $NHR^5$ where $R^5$ represents alkyl of 1–6 carbon atoms, or phenyl optionally substituted by one or more substituents selected from halogen, nitro and alkyl of 1–4 carbon atoms optionally substituted by one or more halogen atoms, which process comprises reacting an amine of formula II or a salt thereof with an isocyanate of formula $R^5NCO$ where $R^5$ is as defined above.

The invention also provides a process for preparing the compound of formula I, which process comprises reacting an amide of formula $R^4CONHR^3$ or a salt thereof (preferably an alkali metal, e.g. the sodium, salt) where $R^3$ and $R^4$ are as in formula I with an amido derivative of formula

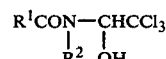

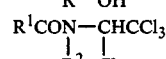

or

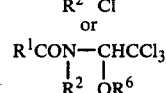

wherein $R^1$ and $R^2$ are as in formula I and $R^6$ represents alkyl of 1–4 carbon atoms.

Almost all the compounds of formula I are new and the invention provides these.

One group of novel compounds consists of those compounds of formula I excluding the compounds in which $R^2$ and $R^3$ each represent a hydrogen atom while $R^1$ and $R^4$ (a) each represent $CH_2F-$ or (b) are different and one of $R^1$ and $R^4$ represents hydrogen, alkyl of up to 9 carbon atoms optionally substituted by one or more substituents selected from halogen and nitro; cycloalkyl of 3–7 carbon atoms; or aryl optionally substituted by one or more substituents selected from halogen and nitro, and the other of $R^1$ and $R^4$ represents alkyl of up to 9 carbon atoms optionally substituted by one or more substituents selected from halogen and nitro; alkenyl of up to 4 carbon atoms optionally substituted by one or more halogen atoms; cycloalkyl of 3–7 carbon atoms; or aryl optionally substituted by one or more substituents selected from halogen and nitro.

A preferred group of novel compounds consists of those compounds of formula I in which one or both of $R^2$ and $R^3$ represents alkyl of up to 9 carbon atoms optionally substituted by one or more substituents selected from halogen, nitro, hydroxy and cyano; cycloalkyl of 3–7 carbon atoms; alkenyl of 2–4 carbon atoms optionally substituted by one or more halogen atoms; alkynyl of 2–4 carbon atoms optionally substituted by one or more halogen atoms; or aryl optionally substituted by one or more substituents selected from halogen, nitro, alkoxy of 1–4 carbon atoms and alkyl of 1–4 carbon atoms optionally substituted by one or more halogen atoms.

Another preferred group of novel compounds consists of those compounds of formula I in which one or both of $R^1$ and $R^4$ represents alkynyl of up to 4 carbon atoms optionally substituted by one or more halogen atoms; a heterocyclic radical optionally substituted by one or more substituents selected from halogen, alkyl of 1-4 carbon atoms and nitro; or amino optionally substituted by one or two substituents selected from alkyl of 1-6 carbon atoms, and phenyl optionally substituted by one or more substituents selected from halogen, nitro and alkyl of 1-4 carbon atoms optionally substituted by one or more halogen atoms.

A further preferred group of novel compounds consists of those compounds of formula I in which one of $R^1$ and $R^4$ represents $CH_3$—, $CF_3$—, $CH_2Cl$— or $CH_3NH$— and the other of $R^1$ and $R^4$ represents hydrogen, trichloromethyl, a heterocyclic radical or phenyl optionally substituted by one or more substituents selected from halogen, nitro, alkoxy of 1-4 carbon atoms and alkyl of 1-4 carbon atoms optionally substituted by one or more halogen atoms. Within this group, particularly preferred are those compounds in which one of $R^1$ and $R^4$ represents $CF_3$— or $CH_2Cl$— and the other of $R^1$ and $R^4$ represents trichloromethyl or phenyl optionally substituted by one or more substituents selected from halogen, nitro, alkoxy of 1-4 carbon atoms and alkyl of 1-4 carbon atoms optionally substituted by one or more halogen atoms.

The group of compounds of formula I in which one or both of $R^1$ and $R^4$ represents trifluoromethyl is also a group of new compounds.

The invention provides a process for preparing the new compounds, which process comprises reacting an amido derivative of formula III with a nitrile of formula $R^4CN$ where $R^4$ is as in formula I.

The invention provides also a process for preparing the new compounds in which $R^1$ and $R^4$ are the same but other than hydrogen, which process comprises reacting chloral with a nitrile of formula $R^4CN$ where $R^4$ is as in formula I.

The present compounds are outstandingly active as fungicides, i.e. in combating fungus, and this activity is of a special and unusual type. As is demonstrated in the Examples, the compounds can protect plants from the adverse effects of fungus even when the mycelial growth of the fungus is not significantly controlled. This is very surprising; many conventional fungicide screens, in which compounds are tested as to their ability to kill fungus, might well have dismissed the present compounds as being of no possible commercial value against fungus.

The present compounds may be salts of the chloral derivative and these may be prepared in conventional ways. Salts with alkalis, e.g. ammonium, alkali metal, alkaline earth metal, or other metal, salts such as sodium salts, may be prepared by reaction of the derivative with alkalis e.g. alkali metal hydroxides such as sodium hydroxide. Salts with acids, e.g. hydrochlorides, may be prepared by reaction of the derivative with acids, e.g. dry hydrogen chloride.

When a symbol in formula I involves a substituted alkyl radical, the alkyl radical is usually substituted by 1, 2 or 3 substituents; where there is more than one substituent, these are preferably the same and preferably are halogen. Preferred substituted alkyl radicals are the alkyl radicals substituted by halogen, e.g. $CH_2Cl$—, $CF_3$— or $CCl_3$—.

Because of mammalian toxicity problems associated with monofluoroacetic acid and its derivatives, however, it is preferred that $R^1$ and $R^4$ be other than $CH_2F$—.

When a symbol in formula I involves a substituted alkenyl or alkynyl radical, the radical is usually monosubstituted by halogen e.g. chlorine.

Any halogen (i.e. fluorine, chlorine, bromine or iodine) in the symbols is preferably fluorine, chlorine or bromine.

When a symbol involves a substituted aryl group, the aryl group is usually substituted by 1 or 2 substituents; where there is more than one substituent, these are preferably the same and preferably are halogen. Preferred substituted aryl groups are phenyl substituted by a methyl, t-butyl, nitro, chloro, bromo or trichloromethyl group or di-substituted by chlorine.

The heterocyclic radical which $R^1$ or $R^4$ may represent is usually a ring of 5 or 6 atoms of which 4 or 5 are carbon atoms and 1 or 2 are hetero atoms selected from nitrogen, oxygen and sulphur, the heterocyclic radical being linked by one of the carbon atoms.

When the heterocyclic radical is substituted, this is usually by 1, 2 or 3 substituents.

Particularly active are those compounds whose chloral derivatives are specifically identified in the Examples. All are new compounds. Particularly preferred is 1,1,1-trichloro-2-benzamido-2-(chloroacetamido)ethane;

1,1,1-trichloro-2-(furan-2-carboxamido)-2-(chloroacetamido)ethane;

1,1,1-trichloro-2-formamido-2-(3-methylureido)ethane;

1,1,1-trichloro-2-(trifluoroacetamido)-2-(trichloroacetamido)ethane; or 1,1,1-trichloro-2-formamido-2-(N-methylamido)ethane; and salts thereof, especially the first two and their salts.

The present compounds are preferably prepared under ambient pressure. Though a starting material may be a salt, it is prefered that the non salt form be employed.

The acylation of the amine of formula II or salt thereof is usually carried out in an inert solvent e.g. acetone. The reaction is suitably conducted at a temperature from $-5°$ to $150°$ C. When the acylating agent is the acid chloride of formula $R^4COCl$, the reaction is preferably conducted in the presence of a base e.g. triethylamine.

The reaction of the amine of formula II or salt thereof with the isocyanate of formula $R^5NCO$ is also usually carried out in an inert solvent e.g. acetone. The reaction is suitably conducted at a temperature from $-5°$ to $150°$ C. Preferably the reaction is conducted in the presence of a base e.g. triethylamine.

The reaction of the amide of formula $R^4CONHR^3$ or salt thereof with an amido derivative of formula III, IV or V may be carried out with or without inert solvent e.g. acetone. The reaction is suitably carried out at $-40°$ to $250°$ C., e.g. $20°-150°$ C. Heating is prefered when the amido derivative is of formula III or V.

The present compounds may also be prepared by the reaction of an amido derivative of formula III with a nitrile of formula $R^4CN$. The reaction is preferably carried out in acid solution especially sulphuric acid e.g. of 65-100% by weight. The reaction may for example be carried out at $0°-100°$ preferably $0°-50°$ C.

Those compounds in which $R^1$ and $R^4$ are the same (but other than hydrogen) may also be prepared by reacting chloral with a nitrile of formula $R^4CN$. The reaction may be carried out with or without an inert solvent. Heat may be desirable to initiate the reaction.

The reaction is suitably conducted at a temperature of 20°–100° C.

The present-compounds are usually employed in the form of compositions containing the active compounds. Usually compositions are initially produced in the form of concentrates, e.g. containing 5–80%; e.g. 10–80% active compound, and these are diluted with water or a hydrocarbon, usually water, for application, e.g. so that the concentration of active compound is 0.01–0.5%. Parts, proportions and percentages in this specification are by weight unless otherwise indicated. The present fungicidal composition may be however a plant growing medium, particularly a peat based plant growing medium, incorporating the active compound usually in amount 10–1000g per $m^3$.

The present compositions normally contain a carrier and/or a surface active agent. The concentrates usually contain a surface active agent distributed uniformly throughout. The surface active agent usually constitutes at least 1%, e.g. at least 2%, of the concentrate.

The carrier may be a liquid, e.g. water (e.g. water used to dilute a concentrate for application). If water is employed as carrier in a concentrate, an organic solvent may also be present as carrier, though this is not usually employed. A surface active agent may advantageously be present. In one embodiment, the compound is ground with water, a wetting agent and a suspending agent, usually is an agitated ball mill containing grinding media, e.g. steatite balls, to a particle size preferably less than 5 microns, to form a flowable suspension concentrate.

The carrier may be a liquid other than water, for example an organic solvent, usually a water-immiscible solvent, e.g. a hydrocarbon which boils within the range 130°–270° C., in which the compounds are dissolved or suspended. A concentrate containing an organic solvent suitably also contains a surface active agent so that the concentrate acts as a self-emulsifiable oil on admixture with water. In a particular method, an emulsifiable concentrate is produced by stirring together, preferably with warming to aid dissolution, the compound, one or more emulsifiers and a water-immiscible solvent to form a solution, and usually filtering or centrifuging to remove insoluble impurities.

The composition may be in the form of an aerosol composition, containing a propellant, which is suitably a polyhalogenated alkane such as dichlorodifluoromethane, and usually containing also a solvent.

The carrier is preferably a solid, which may be finely divided. Examples of suitable solids are peat, fertilizers, clays, sand, limestone, mica, chalk, attapulgite, diatomite, perlite and sepiolite, and synthetic solid carriers, e.g. silicas, silicates and lignosulphonates.

Wettable powders rapidly dispersible in water may be formed by admixing the compound in particulate form with a particulate carrier or spraying molten compound on to the particulate carrier, admixing a wetting agent and a dispersing agent therewith, and fluid energy milling or pulverising the whole powder mixture to a particle size sufficiently small that the wettable powder in use can form the desired suspension.

Granules may be formed by impregnating an absorbent granule base with a solution of the compound and then evaporating off the solvent, or by coating a non-absorbent granule base with a sticker, then with the compound and, preferably, finally with a flowability agent.

The carrier may be a fertilizer.

The term 'surface active agent' is used in the broad sense to include materials variously called emulsifying agents, dispersing agents and wetting agents. Such agents are well known in the art.

The suface active agents used may comprise anionic surface active agents, for example soaps, fatty sulphate esters such as dodecyl sodium sulphate, octadecyl sodium sulphate and cetyl sodium sulphate, fatty aromatic sulphonates such as alkyl-benzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise non-ionic surface active agents, for example condensation products of fatty acids, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide.

The surface active agents may also comprise cationic surface active agents, for example cetyl trimethylammonium bromide.

Preferred surface active agents include fatty alkyl sulphates, alkyl aryl sulphonates, fatty alkyl ethoxylates, sulphated fatty alkyl ethoxylates, dialkyl sulphosuccinate esters, lignin sulphonate salts, sulphonated naphthalene-formaldehyde condensates and sulphonated urea-formaldehyde condensates.

The present compounds can be used in sequence with or in admixture with another pesticide particularly an insecticide and/or another fungicide, especially a fungicide whose spectrum of activity at the particular locus treated is complementary rather than similar. For instance, for use in combating fungus in a crop, the present compound can be used for combating the range of fungal species against which it exhibits good activity and another fungicide can be employed which exhibits good activity against other fungal species to which the crop is susceptible.

Mixtures with other fungicides are particularly useful.

The present compounds are particularly useful against Phycomycetous fungi, especially those which survive in soil and attack plant roots and stems. Good control of Pythium and Phytophthora species, e.g. *Pythium ultimum*, has been achieved. The compounds can be used in association with fungicides which exhibit good activity against other groups e.g. Rhizoctonia spp (e.g. for use on cotton particularly as a seed dressing).

The present commmpounds are particularly useful as seed dressings and can be employed with other seed dressing fungicides.

The compounds are also useful for the soil treatment of plants, e.g. ornamental plants, at the seedling stage and can be employed in association with other fungicides useful at such time.

The compounds may be used in admixture or in sequence with dithiocarbamate fungicides, drazoxolon(4-[2-chlorophenylhydrazono]-3-methyl-5-isoxazolone), etridiazole(5-ethoxy-3-trichloromethyl-1,2,4-thiadiazole) or fenaminosulf(sodium 4-dimethylaminobenzenediazosulphonate).

Preferably mixtures or sequences are with benomyl (methyl 1-[butylcarbamoyl]benzimidazol-2-ylcarbamate), carbendazim (methyl benzimidazol-2-ylcarbamate), thiophanate methyl(1,2-di-[3-methoxycarbonyl- 2-thioureido]benzene), thiabendazole(2-[thiazol-4-yl]benzimidazole), oxycarboxin(2,3-dihydro-6-methyl-5-phenylcarbamoyl-1,4-oxathiin 4,4-dioxide), ethirimol(5-butyl-2-ethylamino-4-hydroxy-6-methylpyrimidine), tridemorph(2,6-dimethyl-4-tridecylmorpholine), daconil (tetrachloroisophthalonitrile), phenylmercuric acetate, sulphur, prothiocarb (S-ethyl N-(3-dimethylaminopropyl)thiocarbamate) or a salt thereof, e.g. the hydrochloride, triadimefon(1-[4-chlorophenoxy]-3,3-dimethyl-1-[1,2,4-triazol-1-yl]-2-butanone) or quintozene(pentachloronitrobenzene). For example mixtures with quintozene may be used as soil treatments at the seedling stage of plants e.g. ornamentals.

The compounds may be used in admixture or in sequence with insecticides such as bendiocarb (2,2-dimethyl-1,3-benzodioxol-4-yl methylcarbamate), aldicarb (2-methyl-2-(methylthio)propionaldehyde O-methylcarbamoyloxime), carbofuran (2,3-dihydro-2,2-dimethyl-7-benzofu anyl methylcarbamate), terbufos (S-tert-butylthiomethyl O,O-diethyl phosphorodithioate), phorate, (O,O-diethyl S-ethylthiomethyl phosphorodithioate), disulfoton (O,O-diethy S-2-ethylthioethyl phosphorodithioate), dimethoate (O,O-dimethyl S-methylcarbamoylmethyl phosphorodithioate), 3,3-dimethyl-1-methylthio-2-butanone O-methylcarbamoyloxime, acephate (O,S-dimethyl acetylphosphoramidothioate) or methomyl (1-[methylthio]ethylideneamino methylcarbamate).

Usually the proportions of present compound to second pesticide are in the range 1:5 to 5:1, e.g. 3 parts of 1,1,1-trichloro-2-benzamido-2-(chloroacetamido)ethane or 1,1,1-trichloro-2-formamido-2-(N-methylacetamido)ethane to 1 part of second pesticide e.g. quintozene.

The present compositions can be formed by admixing the ingredients.

The present compounds may be applied to a locus which is already infested or to a locus to inhibit or prevent infestation. They can be applied to plants, the soil (using the term to include compost), land, aquatic areas, animals, building or furniture surfaces or inanimate materials such as paper, leather, textiles or wood. They can be used to protect stored products.

The compounds show surprising activity as fungicides. They are particularly useful for combating fungal diseases of plants. Thus they are preferably applied to a locus at which a plant is growing or is to grow. They may be applied before or after emergence of the plant or may be applied with seed on sowing, or incorporated into the water used for planting such crops as tobacco. They may be used in hydroponic culture or nutrient film technique. They may be incorporated into a liquid in which seeds are pregerminated prior to fluid sowing. They are especially useful against damping off diseases and hence are especially useful in the early stages of growth of a plant. The compounds are active as fungicides over a wide pH range. For example 1,1,1-trichloro-2-benzamido-2-(2-chloroacetamido)ethane is active against *Pythium ultimum* at pH 4-8, the range in which the fungus lives naturally. Systemic activity in plants has been shown e.g. by 1,1,1-trichloro-2-benzamido-2-(chloroacetamido)ethane or salts thereof. The compounds are preferably used against fungal diseases of crops; these can be agricultural or horticultural crops. The crops may be food crops e.g. legumes such as peas and beans e.g. French beans, soya beans, potatoes, lettuce, cucurbits e.g. cucumbers, squash and melons, tomatoes, brassicas, strawberries, sugarbeet or cereals e.g. wheat, barley, oats, maize or rice. The crops may also be non food crops e.g. cotton, tobacco or ornamentals e.g. bulbs such as tulip, narcissus, daffodil, iris, crocus and amaryllis, bedding plants (such as asters, antirrhinums and stocks), pot plants and container shrubs and trees such as ericas, cupressus, Chamaecyparis and other conifers. The compounds may be used on transplants.

The compounds may be employed as fungicides e.g. plant fungicides in conventional ways. They may be employed for instance at a rate of 0.3–10kg per hectare e.g. to a locus at which plants are growing. The compounds can be applied in solution or suspension to the soil, using the term to include compost, in which plants are growing or are to grow, particularly where the plants are at the seedling stage e.g. of ornamentals; the compounds can be applied thus for example at a concentration of 0.01–0.5% e.g. 0.05–0.5% in the solution or suspension based on applying 5 liters of solution or suspension per square meter. The compounds can be incorporated into a plant growing medium, particularly a peat based plant growing medium, in which plants are to grow, e.g. at a rate of 10–1000 preferably 50–500g e.g. 50–100g of compound per cubic meter. In a preferred embodiment, the compounds are employed as seed dressings, 'seeds' being used in its wider sense as including tubers and bulbs. For this use, the compounds can be employed at a rate for example of 0.1–1g per kg of seed and are preferably used in admixture with a carrier to facilitate admixture with the seed; the carrier can be a liquid, e.g. a hydrocarbon, or a solid, e.g. a clay or Fullers earth.

The invention is illustrated by the following Examples, in which temperatures are in degrees Centigrade.

EXAMPLE 1

Benzoyl chloride (4.7g) in acetone (5ml) was added dropwise to a solution of 1,1,1-trichloro-2-amino-2-(chloroacetamido)ethane (8g) in acetone (50ml) containing triethylamine (3.4g). The temperature rose to 50°. The mixture was stirred for 2 hours. The salt was filtered off and the filtrate poured into water. The solid formed was collected, washed with water and dried (10g). Recrystallisation from nitromethane gave pure 1,1,1-trichloro-2-benzamido-2-(chloroacetamido)ethane (8.7g. m.p. 211°–213°).

Found: C, 38.05; H, 2.74; N, 8.08; $C_{11}H_{10}Cl_4N_2O_2$ requires: C, 38.4; H, 2.93; N, 8.14%.

EXAMPLE 2

Chloroacetyl chloride (79g) in acetone (100 ml) was added dropwise to a solution of 1,1,1-trichloro-2-amino-2-(benzamido)ethane (170g) in acetone (500 ml) containing triethylamine (64.2g). The mixture was stirred for 2 hours. The reaction mixture was poured into water (750 ml). The solid was collected, washed with water and dried (195g). Recrystallisation from nitromethane (or dioxane) gave pure 1,1,1-trichloro-2-benzamido-2-(chloroacetamido)ethane (156g, m.p. 210°–213°)

Found: C, 37.99; H, 3.00; N, 7.99; $C_{11}H_{10}Cl_4N_2O_2$ requires: C, 38.4; H, 2.93; N, 8.14%.

EXAMPLE 3

2-Furoyl chloride (3.3g) in acetone (5 ml) was added dropwise to a solution of 1,1,1-trichloro-2-amino-2-(chloroacetamido)ethane (6g) in acetone (50 ml) containing triethylamine (2.6g). The mixture was stirred for 2 hours, and the triethylamine hydrochloride formed was filtered off. The filtrate was evaporated to leave an oil. The oil was washed with ether and finally triturated with water to give a brown solid (3.35g). Recrystallisation from toluene petrol gave pure 1,1,1-trichloro-2-(chloroacetamido)-2-(2-furamido)ethane (2.6g, m.p. 150-2).

Found: C, 31.99; H, 2.40; N, 8.41; $C_9H_8Cl_4N_2O_3$ requires: C, 32.36, H, 2.41; H, 8.39%.

EXAMPLES 4–13

Following the procedure of Examples 1-3, the following compounds were prepared similarly.

chloro-2-(trichloroacetamido)-2-aminoethane (6.2g) in acetone (50 ml). A few drops of triethylamine were added and the mixture stirred at room temperature for 2 hours. The mixture was finally heated gently at reflux for 1¾ hour, then left overnight at room temperature. The reaction solution was evaporated to dryness to give a pale coloured solid (7.3g). Recrystallisation from aqueous ethanol gave crystals of 1,1,1-trichloro-2-trichloroacetamido-2-(3-methylureido)ethane (4.5g, m.p. 209°–210°)

Found: C, 19.42, H, 1.72, N, 11.27; $C_6H_7Cl_6N_3O_2$ requires: C, 19.69, H, 1.93, N, 11.49%.

$$R^1-CONR^2-\overset{\overset{CCl_3}{|}}{CH}-NH-COR^4 \qquad (VI)$$

| Chloride used | $R^1$ | $R^2$ | $R^4$ | mp | Found, % C | H | N | Requires, % C | H | N |
|---|---|---|---|---|---|---|---|---|---|---|
| $CH_3COCl$ | $CH_3$ | $CH_3$ | H | 126-8° | 28.81 | 3.69 | 11.09 | 29.11 | 3.66 | 11.32 |
| $CCl_3COCl$ | $CF_3$ | H | $CCl_3$ | 150-2° | 17.57 | 0.50 | 6.76 | 17.80 | 0.75 | 6.92 |
| 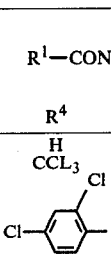 | $CF_3$ | H | 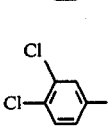 | 171-3° | 30.23 | 1.86 | 6.23 | 30.55 | 1.40 | 6.48 |
| 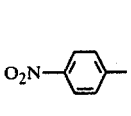 | $CF_3$ | H | 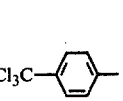 | 207-9° | 30.64 | 1.58 | 6.68 | 30.55 | 1.40 | 6.48 |
| 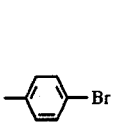 | $CF_3$ | H | 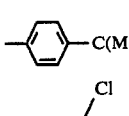 | 224-6° | 32.23 | 1.84 | 10.63 | 32.34 | 1.73 | 10.29 |
| 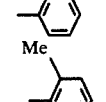 | $CF_3$ | H | 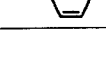 | 168-8° | 30.21 | 1.69 | 5.58 | 29.97 | 1.47 | 5.83 |
|  | $CH_2Cl$ | H |  | 230-2° | 30.84 | 2.10 | 6.75 | 31.24 | 2.15 | 6.75 |
|  | $CF_3$ | H |  | 148-52° | 43.26 | 4.06 | 6.67 | 42.93 | 3.84 | 6.68 |
|  | $ClCH_2$ | H |  | 168-70° | 34.52 | 2.20 | 7.85 | 34.91 | 2.40 | 7.40 |
|  | $ClCH_2$ | H |  | 179-81° | 39.93 | 3.54 | 7.85 | 40.25 | 3.38 | 7.85 |

EXAMPLE 14

A mixture of 1,1,1-trichloro-2-methylamino-2-formamidoethane (6.85g) and acetic anhydride (17ml) was heated on a water bath for 1½ hours. The reaction mixture was concentrated to give a oily residue which was triturated with water. The solid formed was collected, washed with water and dried (3.6g). Recrystallisation from benzene gave pure 1,1,1-trichloro-2-formamido-2-(N-methylacetamido)ethane (3.2g, m.p. 126-8)

Found: C 28.81, H 3.69, N 11.09; $C_6H_9Cl_3N_2O_2$ requires: C 29.11, H 3.66, N 11.32%.

EXAMPLE 15

A solution of methyl isocyanate (2g) in acetone (10 ml) was added, dropwise at 5°, to a solution of 1,1,1-tri-

EXAMPLES 16 & 17

Similarly to Example 15 the following compounds were prepared using the corresponding amino compound and isocyanate. 1,1,1-Trichloro-2-formamido-2-(3-methylureido)ethane (m.p. 215 - 6)

Found: C, 23.69; H, 3.59; N, 16.48; $C_5H_8Cl_3N_3O_2$ requires: C, 24.16; H, 3.24; N, 16.91%.

1,1,1-Trichloro-2-trifluoroacetamido-2-[3-(3,4-dichlorophenyl)-ureido]ethane (m.p. 276°-8°)

Found: C, 29.34; H, 1.76; N, 9.13; $C_{11}H_7Cl_5F_3N_3O_2$ requires: C, 29.52; H, 1.58; N, 9.39%.

EXAMPLE 18

Benzonitrile (5.2g) was added dropwise to a solution of 1,1,1-trichloro-2-hydroxy-2-(chloroacetamido)ethane (12.05g) in concentrated sulphuric acid (50 ml). The temperature was kept at 0° during the addition. The mixture was stirred at room temperature for 4 hours, then left overnight. The reaction mixture was poured on to ice. The precipitated solid was collected, washed with water and dried (19.6g). Recrystallisation from nitromethane gave pure 1,1,1-trichloro-2-benzamido-2-(chloroacetamido)ethane (14.6g, m.p. 210°–12°)

Found: C, 38.24%, H, 2.7%; N, 8.16%; $C_{11}H_{10}Cl_4N_2O_2$ requires: C, 38.4%; H, 2.93%; N, 8.14%.

EXAMPLE 19

Chloroacetonitrile (4.1g) was added dropwise to a solution of 1,1,1-trichloro-2-hydroxy-2-benzamidoethane (13.4g) in concentrated sulphuric acid (50 ml). The temperature was kept at 0° during the addition. The mixture was stirred at room temperature for 4 hours, then left overnight. The reaction mixture was poured on to ice. The precipitated solid was collected, washed with water and dried (14.65g). Recrystallisation from nitromethane gave pure 1,1,1-trichloro-2-benzamido-2-(chloroacetamido)ethane (12.7g, m.p. 210°–12°) whose infra red spectrum was identical to that of the product of the preceding Example.

EXAMPLE 20

A 50% wettable power was prepared by mixing and fluid energy milling ("micronising"):

| | |
|---|---|
| 1,1,1-trichloro-2-benzamido-2-(chloroacetamido)ethane | 50% |
| Arkopon T highly concentrated (64% sodium oleoyl N-methyl tauride) | 7.5% |
| china clay | 42.5% |

EXAMPLES 21-23

One week old maize meal/sand culture of the damping off disease organism *Pythium ultimum*, or two week ole maize/sand culture of the damping off disease organism *Rhizoctonia solani*, was thoroughly mixed by hand with clean sterile John Innes No 1 potting compost in the ratio of 3 kg of the Pythium culture to 12 liters of soil or 1.5 kg of the Rhizoctonia culture to 14 liters of soil. The infected soil was then left for approximately 18 hours before use.

The test compound listed in the Table below was ground together with the non-ionic wetting agent Tween 20 (polyoxyethylene sorbitan monolaurate prepared from 20 moles of ethylene oxide) (1% of final volume) until a solution or fine suspension was produced which was then diluted with distilled water to give 160 ml of solution containing 1500, 500, 150 or 50 parts per million of the test compound. 15 ml aliquots of this solution were added to 75g portions of the infected soil which was contained in small plastic cartons 60 mm diameter × 55 mm high.

Fifteen cabbage seeds, variety Flower of Spring, were placed in a circular depression in the treated infected soil, recovered, and the whole sealed with a plastic cap. These were then placed in a constant temperature room at 25° C. ± 1° C. Four replications per treatment were made together with controls where no disease organism and no test compound were employed and where the disease organism but no test compound was employed.

After six days, the cartons were removed from the controlled temperature chamber and assessed for degree of fungal growth on the soil surface, M (measured as the percentage of mycelial control based on the mycelial control in the experiment employing disease organism but no test compound being 0%), and percentage of seedling emergence, G (measured as the percentage germination based on the germination in the experiment employing no disease organism and no test compound being 100%).

The results obtained were:

| Example | Compound | Dose Rate,ppm of the soil | P ultimum M, % | P ultimum G, % | R solani M, % | R solani G, % |
|---|---|---|---|---|---|---|
| 21 | 1,1,1-trichloro-2-benzamido-2-(chloroacetamido)ethane | 300 | 73 | 94 | — | — |
| | | 100 | 11 | 82 | — | — |
| | | 30 | 0 | 100 | — | — |
| | | 10 | 0 | 85 | — | — |
| 22 | 1,1,1-trichloro-2-(furan-2-carboxamido)-2-(chloroacetamido)-ethane | 100 | 0 | 91 | — | — |
| | | 30 | 35 | 70 | — | — |
| | | 10 | 0 | 100 | — | — |
| 23 | 1,1,1-trichloro-2-formamido-2-(N-methylacetamido)ethane | 100 | 20 | 86 | 0 | 97 |
| | | 30 | 0 | 33 | 0 | 47 |

No damage of the germinated plants was observed in these Examples.

In a control where the soil was inoculated with the disease organism but not treated with test compound, no germination occurred.

These results show that the compounds give good protection against the damping off organism while not appreciably controlling mycelial growth.

EXAMPLE 24

Cultures of *Pythium ultimum* were produced in maize meal/stand over a period of 10 days and were incorporated into Levington potting compost at the rate of 1:3. This inoculated soil was placed in two pots of diameter 57 mm. 15 cabbage seeds (variety Primo Golden Acre) were sown in each pot and the chemical 1,1,1-trichloro-2-benzamido-2-(chloroacetamido)ethane was then sprayed on as a suspension in water of the formulation of Example 20 to give a concentration in the soil shown in the Table below, 15 ml of the suspension being applied to each pot. Each treatment was replicated four times, and for comparison a control was run using the inoculated soil but without chemical treatment.

The percentage germination based on a control using no disease organism and no chemical treatment giving 100% germination was:

| Parts per million of soil | % Germination |
|---|---|
| 100 | 80 |
| 75 | 82 |
| 50 | 85 |
| 40 | 78 |
| 30 | 48 |
| 20 | 68 |
| Inoculated Control | 2 |

EXAMPLE 25

Pythium cultures were grown in maize meal/sand for a period of 10 days before being incorporated into Levington potting compost at a rate of 1:400. The inoculated soil was placed in half a seed tray and 24 hours after the inoculation 100 pea seeds (variety Onward) were sown in the soil. The chemical 1,1,1-trichloro-2-benzamido-2-(chloracetamido)ethane was then sprayed on as a suspension in water of the formulation of Example 20 to give a concentration in the soil of 50 or 100 parts per million, 150 ml of the suspension being applied. Each treatment was replicated 4 times, and for comparison a control was run using the inoculated soil but without chemical treatment.

The percentage germination based on a control using no disease organism and no chemical treatment giving 100% germination was:

| Parts per million of soil | % Germination |
|---|---|
| 50 | 120 |
| 100 | 110 |
| Inoculated Control | 46 |

EXAMPLES 25-30

Aqueous acetone solutions or suspensions containing 500 or 125 parts per million weight/volume of the compound listed in the table below, and 125 parts per million of the wetting agent Lissapol NX (a condensate of nonyl phenol with ethylene oxide), were applied to run off to the leaves of yound potato plants having seven fully explained leaves. The treated plants, together with controls treated with wetting agent along, were inoculated 24 hours after the chemical application with an aqueous suspension of sporangia of the disease organism known as potato blight *Phytophthor infestants*. The plants were then placed in a water saturated atmosphere for 24 hours and then transferred to a controlled environment room (18° C. and 80–90% relative humidity) until disease incidence was measured 5 days later. The percentage disease control, compared to less than 5% on the controls, was:

| Example | Compound | % Disease Control 500 ppm | 125 ppm |
|---|---|---|---|
| 25 | 1,1,1-trichloro-2-benzamido-2-(chloroacetamido)ethane | 94 | 70 |
| 26 | 1,1,1-trichloro-2-trifluoroacetamido-2-(trichloroacetamido)ethane | 98 | 70 |
| 27 | 1,1,1-trichloro-2-chloroacetamido-2-(o-methylbenzamido)ethane | 85 | 80 |
| 28 | 1,1,1-trichloro-2-chloroacetamido-2-(m-chlorobenzamido)ethane | 84 | 70 |
| 29 | 1,1,1-trichloro-2-trifluoroacetamido-2-(p-t-butylbenzamido)ethane | 84 | 75 |
| 30 | 1,1,1-trichloro-2-formamido-2-(p-bromobenzamido)ethane | 84 | — |

EXAMPLE 31

*Pythium ultimum* cultures were set up in maize meal/sand 1 week before compost was inoculated with the fungus by mixing the cultures with compost in a small cement mixer for 10 minutes, 1 part of culture (approximately 300 ml) being mixed with 40 parts of compost (approximately sufficient for eighty 64 mm diameter pots). The inoculated compost was then potted up in 64 mm diameter pots and these were each drenched with 16 ml of a suspension of 1,1,1-trichloro-2-benzamido-2-(chloroacetamido)ethane prepared by admixing the 50% wettable powder of Example 20 with water. The suspension contained the parts per million (ppm) of the compound listed in the Tables below. Seeds of aster (Giant Princess mixed), antirrhinum (FI hybrid nanum carioca hybrids mixed) and stocks (100% double type dwarf ten week mixed) were sown 40 to a pot. The pots were watered from the bottom and stored in a cold controlled environment room at 10° C., light/dark, 24 hours. Until the seeds had germinated, all light was kept off by means of black polythene and newspaper. Germination was assessed after 3–4 weeks. Plant vigour was also assessed. The results are shown in the following Tables:

| | Percent Germination | | |
|---|---|---|---|
| | Percent Germination in Inoculated Compost | | |
| Treatment | Aster | Antirrhinum | Stock |
| 200 ppm | 52 | 71 | 79 |
| 100 ppm | 61 | 70 | 81 |
| 50 ppm | 65 | 63 | 82 |
| Control | 42 | 58 | 60 |

| | Plant Vigour | | |
|---|---|---|---|
| | Plant Vigour expressed as % of Uninoculated Control | | |
| Treatment | Aster | Antirrhinum | Stock |
| 200 ppm | 96 | 80 | 106 |
| 100 ppm | 135 | 102 | 96 |
| 50 ppm | 106 | 84 | 95 |
| Inoculated Control | 92 | 62 | 74 |

EXAMPLE 32

In a pot experiment, *Phytophthora cinnamomi* (wilt of *Chamaecyparis lawsoniana* variety ellwoodii) was well controlled by 1,1,1-trichloro-2-benzamido-2-(chloroacetamido)ethane.

EXAMPLE 33

Mixed maize meal/sand cultures of *Pythium debaryanum* and *Pythium ultimum* were incubated at 22° C. for 7 days. This was then mixed with unsterilised John Innes compost at the ratio of 1 part inoculum to 30 parts compost by volume, and left for 72 hours. To this soil in pots, 1,1,1-trichloro-2-benzamido-2-(chloroacetamido)ethane was applied as 110 ml per pot (equivalent to 5 liters/square meter) of a suspension in water of the 50% wettable powder of Example 20. The suspension contained the number of parts per million (ppm) of the compound, and the soil consequently contained the number of parts per million of the compound, listed in the Table below. Tulip bulbs (variety Apeldoorn) were immediately planted in the soil, and the pots were kept in a 12 hour light/dark cycle at 22° C. After 29 days and 36 days, foliar Pythium attack was assessed. The results are shown below. 10 Bulbs were used per plot and 5 replications per treatment were carried out, randomly distributed in the pots.

| Treatment | | Level of Pythium attack after | |
|---|---|---|---|
| Suspension containing | Soil containing | 29 days | 36 days |
| 1500 ppm | 82.5 ppm | 46 | 44 |
| 1000 ppm | 55.0 ppm | 48 | 48 |
| Untreated Inoculated Control | — | 66 | 70 |

EXAMPLES 34–37

The in vitro activity of 1,1,1-trichloro-2-benzamido-2-(chloracetamido)ethane (compound A) and 1,1,1-trichloro-2-(furan-2-carboxamido)-2-(chloroacetamido)ethane (compound B) against various species of soil inhabiting Phycomycetes, namely *Pythium ultimum, Phytophthora crystogea, P cinnamomi* and *P nicotianae,* was evaluated. The results are shown below.

| Percent Inhibition of Pythium Ultimum | | | | | | |
|---|---|---|---|---|---|---|
| | | Concentration of Compound, ppm | | | | |
| Example | Compound | 1 | 3 | 5 | 10 | 30 |
| 34 | A | 95 | 100 | 100 | 100 | 100 |
| 35 | B | 77 | 100 | 93 | 100 | 96 |
| Percent Average Inhibition of 3 Phythophthora Species | | | | | | |
| | | Concentration of Compound, ppm | | | | |
| Example | Compound | 1 | 3 | 5 | 10 | 30 |
| 36 | A | 38 | 55 | 61 | 76 | 87 |
| 37 | B | 13 | 40 | 59 | 75 | 94 |

EXAMPLE 38

A seed dressing was prepared comprising:

| 1,1,1-Trichloro-2-benzamido-2-(chloroacetamido)ethane | 50% |
|---|---|
| Risella oil 17 (from Shell) | 2% |
| China Clay | to 100% |

The Risella oil was added dropwise to a mixture of the active compound and China Clay and further mixed to produce the seed dressing.

EXAMPLE 30

Pesticides granules were prepared comprising:

| 1,1,1-Trichloro-2-benzamido-2-(chloroacetamido)ethane | 5% |
|---|---|
| Hyvis 05 (from BP Chemicals) | 2.5% |
| Neosyl (from J Crosfield) | 2% |
| Limestone grit, 0.3–0.85 mm in major dimension | to 100% |

The Hyvis was added to the Limestone grit and mixed. The active compound was hammer-milled and added to the mixer, and mixed until it was coated on the base granules. The Neosyl was then added and mixed until the resulting granules flowed freely through a pesticide granule applicator.

EXAMPLE 40

A seed dressing was prepared comprising:
Wettable powder (of Example 20); 96%
Risella oil; 4%
The Risella oil was added dropwise to the wettable powder and thoroughly mixed to form the seed dressing.

We claim:

1. A method of combating fungus, which method comprises applying to a fungus or a lucus subject to infestation thereby a fungicidally effective amount of a compound which is a bis-amide of formula

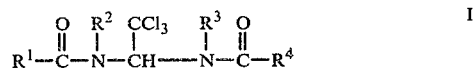

or a salt thereof
wherein $R^1$ and $R^4$ are the same or different and each represents hydrogen; alkyl of up to 9 carbon atoms optionally substituted by one or more substituents selected from the group consisting of halogen, nitro, hydroxy and cyano; alkenyl of up to 4 carbon atoms optionally substituted by one or more halogen atoms; alkynyl of up to 4 carbon atoms optionally substituted by one or more halogen atoms; cycloalkyl of 3–7 carbon atoms; aryl optionally substituted by one or more substituents selected from the group consisting of halogen, nitro, alkoxy of 1–4 carbon atoms and alkyl of 1–4 carbon atoms optionally substituted by one or more halogen atoms; of amino optionally substituted by one or two substituents selected from the group consisting of alkyl of 1–6 carbon atoms, and phenyl optionally substituted by one or more substituents selected from the group consisting of halogen, nitro and alkyl of 1–4 carbon atoms optionally substituted by one or more halogen atoms; and $R^2$ and $R^3$ are the same or different and each represents hydrogen; alkyl of up to 9 carbon atoms optionally substituted by one or more substituents selected from the group consisting of halogen, nitro, hydroxy and cyano; cycloalkyl of 3–7 carbon atoms; alkenyl of 2–4 carbon atoms optionally substituted by one or more halogen atoms; alkynyl of 2–4 carbon atoms optionally substituted by one or more halogen atoms; or aryl optionally substituted by one or more substituents selected from the group consisting of halogen, nitro, alkoxy of 1–4 carbon atoms and alkyl of 1–4 carbon atoms optionally substituted by one or more halogen atoms.

2. A method according to claim 1 wherein the compound is applied to soil in which plants are growing or are to grow.

3. A method according to claim 2 wherein 0.3–10 kg of the compound are applied per hectare.

4. A method according to claim 1 wherein the compound is applied to seeds as a seed dressing.

5. A method according to claim 4 wherein 0.1–1g of the compound is applied per kg of seed.

6. A method according to claim 1, wherein the compound is 1,1,1-trichloro-2-benzamido-2-(chloroacetamido) ethane or a salt thereof.

7. A method according to claim 1, wherein the compound is 1,1,1-trichloro-2-benzamido-2-(chloroacetamido)ethane.

8. A method of combating fungus which comprises applying to a locus a fungicidally effective amount of a compound which is a bis-amide of the formula

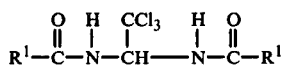

or a salt thereof, wherein the two $R^1$ symbols represent identical radicals selected from the group consisting of hydrogen; alkyl of up to 9 carbon atoms optionally substituted by one or more substituents selected from the group consisting of chlorine, bromine, iodine, nitro, hydroxy and cyano; alkenyl of up to 4 carbon atoms optionally substituted by one or more halogen atoms; alkynyl of up to 4 carbon atoms optionally substituted by one of more halogen atoms; cycloalkyl of 3–7 carbon atoms; aryl optionally substituted by one or more substituents selected from the group consisting of halogen, nitro alkoxy of 1–4 carbon atoms and alkyl of 1–4 carbon atoms optionally substituted by one or more halogen atoms; and amino optionally substituted by one or two substituents selected from the group consisting of alkyl of 1–6 carbon atoms, and phenyl optionally substituted by one or more substituents selected from the group consisting of halogen, nitro and alkyl of 1–4 carbon atoms optionally substituted by one or more halogen atoms.

9. A method of combating fungus which comprises applying to a locus a fungicidally effective amount of a compound which is a bis-amide of the formula

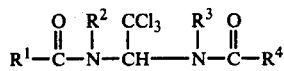 I or a salt thereof
wherein $R^1$ and $R^4$ are the same or different and each represents hydrogen; alkyl of up to 9 carbon atoms optionally substituted by one or more substituents selected from the group consisting of halogen, nitro, hydroxy and cyano; alkenyl of up to 4 carbon atoms optionally substituted by one or more halogen atoms; alkynyl of up to 4 carbon atoms optionally substituted by one or more halogen atoms; cycloalkyl of 3–7 carbon atoms; aryl optionally substituted by one or more substituents selected from the group consisting of halogen, nitro, alkoxy of 1–4 carbon atoms and alkyl of 1–4 carbon atoms optionally substituted by one or more halogen atoms; or amino optionally substituted by one or two substituents selected from the group consisting of alkyl of 1–6 carbon atoms, and phenyl optionally substituted by one or more substituents selected from the group consisting of halogen, nitro and alkyl of 1–4 carbon atoms optionally substituted by one or more halogen atoms;
one of $R^2$ and $R^3$ represents alkyl of up to 9 carbon atoms optionally substituted by one or more substituents selected from the group consisting of halogen, nitro, hydroxy and cyano; cycloalkyl of 3–7 carbon atoms; alkenyl of 2–4 carbon atoms optionally substituted by one or more halogen atoms; alkynyl of 2–4 carbon atoms optionally substituted by one or more halogen atoms; or aryl optionally substituted by one or more substituents selected from the group consisting of halogen, nitro, alkoxy of 1–4 carbon atoms and alkyl of 1–4 carbon atoms optionally substituted by one or more halogen atoms; and
the other of $R^2$ and $R^3$ represents hydrogen or a group as defined for the said first one of $R^2$ and $R^3$.

10. A method of combating fungus which comprises applying to a locus a fungicidally effective amount of a compound which is a bis-amide of the formula

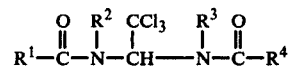 I or a salt thereof
wherein one of $R^1$ and $R^4$ represents alkynyl of up to 4 carbon atoms optionally substituted by one or more halogen atoms; or amino optionally substituted by one or two substituents selected from the group consisting of alkyl of 1–6 carbon atoms, and phenyl optionally substituted by one or more substituents selected from the group consisting of halogen, nitro and alkyl of 1–4 carbon atoms optionally substituted by one or more halogen atoms;
the other of $R^1$ or $R^4$ represents hydrogen; alkyl of up to 9 carbon atoms optionally substituted by one or more substituents selected from the group consisting of halogen, nitro, hydroxy and cyano; alkenyl of up to 4 carbon atoms optionally substituted by one or more halogen atoms; alkynyl of up to 4 carbon atoms optionally substituted by one or more halogen atoms; cycloalkyl of 3–7 carbon atoms; aryl optionally substituted by one or more substituents selected from the group conisting of halogen, nitro, alkoxy of 1–4 carbon atoms and alkyl of 1–4 carbon atoms optionally substituted by one or more halogen atoms; or amino optionally substituted by one or two substituents selected from the group consisting of alkyl of 1–6 carbon atoms, and phenyl optionally substituted by one or more substituents selected from the group consisting of halogen, nitro and alkyl of 1–4 carbon atoms optionally substituted by one or more halogen atoms; and
$R^2$ and $R^3$ are the same or different and each represents hydrogen; alkyl of up to 9 carbon atoms optionally substituted by one or more substituents selected from the group consisting of halogen, nitro, hydroxy and cyano; cycloalkyl of 3–7 carbon atoms; alkenyl of 2–4 carbon atoms optionally substituted by one or more halogen atoms; alkynyl of 2–4 carbon atoms optionally substituted by one or more halogen atoms; or aryl optionally substituted by one or more substituents selected from the group consisting of halogen, nitro, alkoxy of 1–4 carbon atoms and alkyl of 1–4 carbon atoms optionally substituted by one or more halogen atoms.

11. A method of combating a fungus which comprises applying to a locus a fungicidally effective amount of a compound which is a bis-amide of the formula

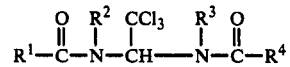 I or a salt thereof
wherein one of $R^1$ and $R^4$ repesents $CH_3-$, $CF_3-$, $CH_2Cl-$ or $CH_3NH-$ and the other of $R^1$ or $R^4$ represents hydrogen, trichloromethyl or phenyl optionally substituted by one or more substituents selected from the group consisting of halogen, nitro, alkoxy of 1–4 carbon atoms and alkyl of 1–4 carbon atoms optionally substituted by one or more halogen atoms; and $R^2$ and $R^3$ are the same or different and each represents hydrogen; alkyl of up to 9 carbon atoms optionally substituted by one or more substituents selected from the group consisting of halogen, nitro, hydroxy and cyano; cycloalkyl of 3–7 carbon atoms; alkenyl of 2–4 carbon atoms optionally substituted by one or more halogen atoms; alkynyl of 2–4 carbon atoms optionally substituted by one or more halogen atoms; aryl optionally substituted by one or more substituents selected from the group consisting of halogen, nitro, alkoxy or 1–4 carbon atoms and alkyl of 1–4 carbon atoms optionally substituted by one or more halogen atoms.

12. A method according to claim 11 in which one of $R^1$ and $R^4$ represents $CF_3$— or $CH_2Cl$— and the other of $R^1$ and $R^4$ represents trichloromethyl, or phenyl optionally substituted by one or more substituents selected from the group consisting of halogen, nitro, alkoxy of 1–4 carbon atoms and alkyl of 1–4 carbon atoms optionally substituted by one or more halogen atoms.

13. A method of combating a fungus which comprises applying to locus a fungicidally effective amount of a compound which is a bis-amide of the formula

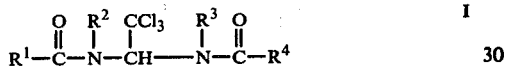

or a salt thereof
wherein one of $R^1$ and $R^4$ represents trifluoromethyl; the other of $R^1$ or $R^4$ represents hydrogen; alkyl of up to 9 carbon atoms optionally substituted by one or more substituents selected from the group consisting of halogen, nitro, hydroxy and cyano; alkenyl of up to 4 carbon atoms optionally substituted by one or more halogen atoms; alkynyl of up to 4 carbon atoms optionally substituted by one or more halogen atoms; cycloalkyl of 3–7 carbon atoms; aryl optionally substituted by one or more substituents selected from the group consisting of halogen, nitro, alkoxy of 1–4 carbon atoms and alkyl of 1–4 carbon atoms optionally substituted by one or more halogen atoms; or amino optionally substituted by one or two substituents selected from the group consisting of alkyl of 1–6 carbon atoms, and phenyl optionally substituted by one or more substituents selected from the group consisting of halogen, nitro and alkyl of 1–4 carbon atoms optionally substituted by one or more halogen atoms; and $R^2$ and $R^3$ are the same or different and each represents hydrogen; alkyl of up to 9 carbon atoms optionally substituted by one or more substituents selected from the group consisting of halogen, nitro, hydroxy and cyano; cycloalkyl of 3–7 carbon atoms; alkenyl of 2–4 carbon atoms optionally substituted by one or more halogen atoms; alkynyl of 2–4 carbon atoms optionally substituted by one or more halogen atoms or aryl optionally substituted by one or more substituent selected from the group consisting of halogen, nitro, alkoxy of 1–4 carbon atoms and alkyl of 1–4 carbon atoms optionally substituted by one or more halogen atoms.

14. A fungicidal composition comprising a fungicidally effective amount of a compound which is a bis-amide of formula

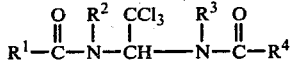

or a salt thereof
wherein one of $R^1$ and $R^4$ repesents $CH_3$—, $CF_3$—, $CH_2Cl$— or $CH_3NH$— and the other of $R^1$ and $R^4$ represents hydrogen, trichloromethyl or phenyl optionally substituted by one or more substituents selected from the group consisting of halogen, nitro, alkoxy of 1–4 carbon atoms and alkyl of 1–4 carbon atoms optionally substituted by one or more halogen atoms; and $R^2$ and $R^3$ are the same or different and each represents hydrogen; alkyl of up to 9 carbon atoms optionally substituted by one or more substituents selected from the group consisting of halogen, nitro, hydroxy and cyano; cycloalkyl of 3–7 carbon atoms; alkenyl of 2–4 carbon atoms optionally substituted by one or more halogen atoms; alkynyl of 2–4 carbon atoms optionally substituted by one or more halogen atoms; or aryl optionally substituted by one or more substituents selected from the group consisting of halogen, nitro, alkoxy of 1–4 carbon atoms and alkyl of 1–4 carbon atoms optionally substituted by one or more halogen atoms, together with at least one material selected from the group consisting of carriers and surface active agents.

15. A composition according to claim 14, in which the carrier is a peat based plant growing medium.

16. A composition according to claim 15 which contains 10–1,000g of the bis-amide compound per cubic meter.

17. A composition according to claim 14, wherein the compound is 1,1,1,-trichloro-2-benzamido-2-(chloroacetamido)ethane or a salt thereof.

18. A composition according to claim 17, which contains a surface active agent.

19. A composition according to claim 14, wherein the compound is 1,1,1-trichloro-2-benzamido-2-(chloroacetamido)ethane.

20. A fungicidal composition comprising a fungicidally effective amount of a compound which is a bis-amide of formula

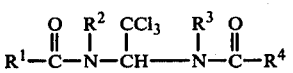

or a salt thereof
wherein $R^1$ and $R^4$ are the same or different and each represents hydrogen; alkyl of up to 9 carbon atoms optionally substiuted by one or more substituents selected from the group consisting of halogen, nitro, hydroxy and cyano; alkenyl of up to 4 carbon atoms optionally substituted by one or more halogen atoms; alkynyl of up to 4 carbon atoms optionally substituted by one or more halogen atoms; cycloalkyl of 3–7 carbon atoms; aryl optionally substituted by one or more substituents selected from the group consisting of halogen, nitro, alkoxy of 1–4 carbon atoms and alkyl of 1–4 carbon atoms optionally substituted by one or more halogen atoms; or amino optionally substituted by one or two substituents selected from the group consisting of alkyl of 1–6 carbon atoms, and phenyl optionally substituted by one or more substituents selected from the group consisting of halogen, nitro and alkyl of 1–4 carbon atoms optionally substituted by one or more halogen atoms; and $R^2$ and $R^3$ are the same or different and each represents hydrogen; alkyl of up to 9 carbon atoms optionally substituted by one or more substituents selected from the group consisting of halogen, nitro, hydroxy and cyano; cycloalkyl of 3–7 carbon atoms; alkenyl of 2–4 carbon atoms optionally substituted by one or more halogen atoms; alkynyl of 2–4 carbon atoms optionally substituted by one or more halogen atoms; or aryl optionally substituted by one or more substituents selected from the group consisting of halogen, nitro, alkoxy of 1–4 carbon atoms and alkyl of 1–4 carbon atoms optionally substituted by one or more halogen atom, together with at least one material selected from the group consisting of solid carriers, liquid carriers which are hydrocarbons of boiling point within the range of 130°–270° C., and surface active agents.

* * * * *